May 21, 1957 D. B. COLE Plant Pat. 1,605
HONEY LOCUST TREE
Filed Aug. 16, 1955
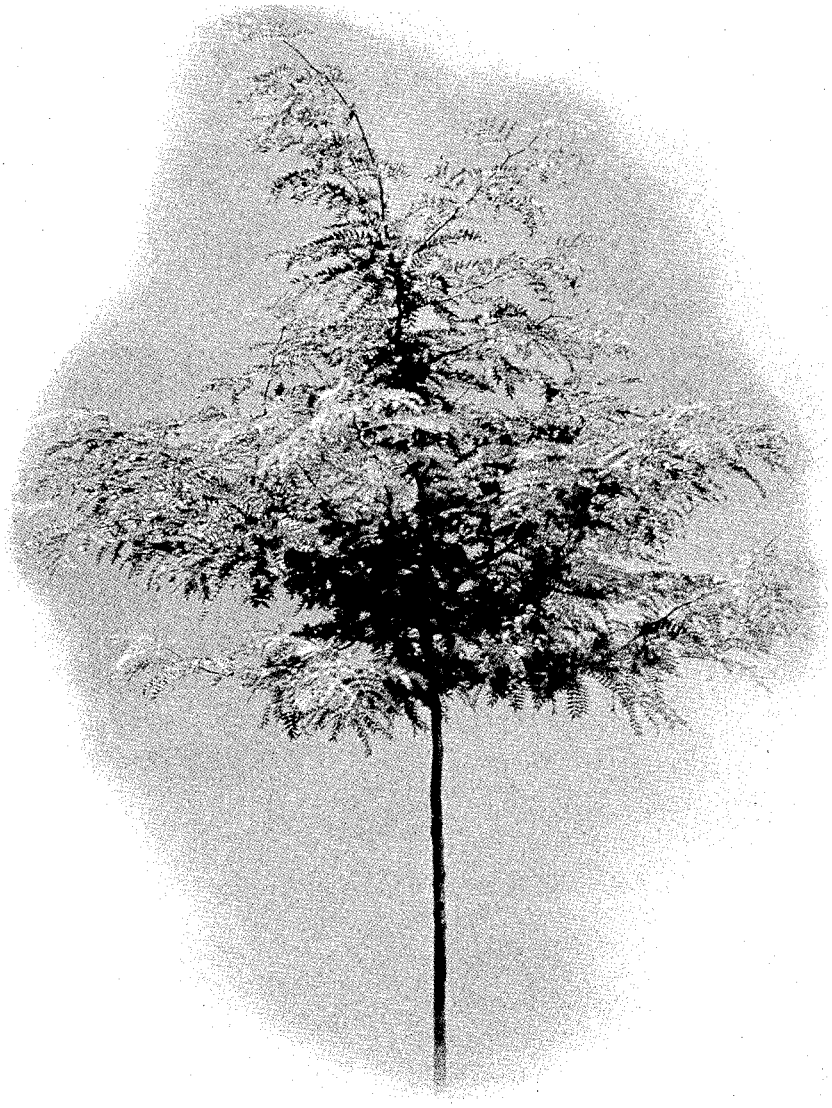
INVENTOR.
DAVID BARRETT COLE
BY
Oberlin & Limbach
ATTORNEYS.

United States Patent Office

Plant Pat. 1,605
Patented May 21, 1957

1,605

HONEY LOCUST TREE

David Barrett Cole, Mentor Township, Lake County, Ohio, assignor to The Cole Nursery Company, Painesville, Ohio, a corporation of Ohio Application August 16, 1955, Serial No. 528,858

1 Claim. (Cl. 47—59)

The present invention relates to a new and distinct variety of honey locust tree, *Gleditsia triacanthos* L., Var. Inermis, originated by me, having a novel habit of growth and other distinguishing characteristics as will be hereinafter more particularly pointed out. The original parent specimen was a seedling grown by me at Painesville, Ohio. Such original parent specimen was discovered by me in a plantation of approximately 10,000 thornless honey locust seedlings grown by me from seed from selected parent trees exhibiting some tendency toward the desired characteristics.

I have propagated my new honey locust tree at Painesville, Ohio, asexually by budding, and the tree can readily be propagated in this manner, perpetuating all of its original characteristics.

As to habit of growth, my new and distinct variety of honey locust tree as indicated by two to five year specimens is characterized by having a straight trunk, uniform closely spaced branches, turning slightly upward at the ends with graceful feathery foliage and a well balanced top. The habit of growth suggests a medium to large tree at maturity, but because of the straight trunk and uniform branching, the trees appear smaller and far more compact than the common thornless honey locust.

The branches emerge from the trunk at nearly 90° angles, conducive to sturdiness, and turn slightly upward at the ends. The branches thus emerge in all radial directions from the trunk and are well spaced, giving as before stated a uniform, well balanced top. Furthermore, the branches are sturdier than those of the common thornless honey locust. The bark on the early current season's growth is medium to dark green, adding brownish coloring as it ages, and is almost free from lenticels. The bark on the twigs is slightly darker than that of the common honey locust. The trees are essentially free from thorns, although occasionally a few short stubby thorns are found on vigorous growth.

Referring to the drawing, the single figure there appearing shows the parent tree in its tenth year of growth, being 12 feet tall, 1⅞ inches caliber. The specimen that is illustrated is less than normal size because of a number of transplantings and because of severe cutting for budwood until about two years prior to taking the picture. For the same reasons, under normal conditions not only would the height and caliper be considerably greater, but the symmetry and density of the lower part of the branch structure would continue to the top.

The mature leaves are 14–28 cm. long and mostly bipinnate. The bipinnate leaves have 8 to 16, mostly 10–14 pinnae. The leaf rachis is grooved and hairy. Some leaves are both simple pinnate and bipinnate. Pinnate leaflets mostly 2.5 to 4.2 cm. long, oblong-laceolate, dark green both above and below, slightly hairy below and with crenate-serrulate margins. Leaves spaced somewhat closer than those on the common thornless honey locust. Leaflets on the bipinnate leaves of approximately the same size as those of the common thornless honey locust. The colors of the foliage and flowers are typical of the common thornless honey locust and are not distinctive.

The flowers of my new variety of honey locust are all male with no fruit being set. However, it is possible that more mature trees may set an occasional seed.

I claim:

A new and distinct variety of substantially thornless honey locust tree, *Gleditsia triacanthos* L., Var. Inermis, having a strong, sturdy, straight trunk, with exceptionally well spaced, wide-spreading branches, said branches emerging from the trunk at nearly 90° angles and turning slightly upward at the ends, the leaflets being slightly hairy below and with crenate-serrulate margins.

No references cited.